United States Patent [19]

Gold et al.

[11] Patent Number: 4,636,346
[45] Date of Patent: Jan. 13, 1987

[54] PREPARING GUIDING CATHETER

[75] Inventors: Jeffrey G. Gold, Miami; Gyan S. Pande, Miramar; Kevin Smith, Miami, all of Fla.

[73] Assignee: Cordis Corporation, Miami, Fla.

[21] Appl. No.: 698,561

[22] Filed: Feb. 6, 1985

Related U.S. Application Data

[63] Continuation-in-part of Ser. No. 587,382, Mar. 8, 1984, Pat. No. 4,596,563, which is a continuation-in-part of Ser. No. 587,557, Mar. 8, 1984, which is a continuation-in-part of Ser. No. 502,526, Jun. 9, 1983, abandoned.

[51] Int. Cl.⁴ .................... B29C 47/06; B29C 63/22
[52] U.S. Cl. ........................ 264/139; 156/248; 264/23; 264/28; 264/149; 264/150; 264/159; 264/173; 264/230; 264/162; 264/248; 264/344; 604/280
[58] Field of Search ............ 264/173, 174, 150, 139, 264/167, 149, 230, 344, 23, 28, 159, 248, 162; 425/132, 133.1; 156/248; 604/280

[56] References Cited

U.S. PATENT DOCUMENTS

| | | | |
|---|---|---|---|
| 3,485,234 | 12/1969 | Stevens | 128/2 |
| 3,508,554 | 4/1970 | Sheridan | 264/209.7 |
| 3,561,493 | 2/1971 | Maillard | 138/141 |
| 3,585,707 | 6/1971 | Stevens | 264/173 |
| 3,618,614 | 11/1971 | Flynn | 128/348 |
| 3,755,525 | 8/1973 | Sheridan et al. | 264/209.3 |
| 3,924,632 | 12/1975 | Cook | 128/348 |
| 4,100,246 | 7/1978 | Frisch | 264/150 |
| 4,182,787 | 1/1980 | Goossens et al. | 428/36 |
| 4,195,637 | 4/1980 | Gruntzig et al. | 128/348 |
| 4,211,741 | 7/1980 | Ostoich | 264/173 |
| 4,219,520 | 8/1980 | Kline | 264/230 |
| 4,250,072 | 2/1981 | Flynn | 260/31.2 N |
| 4,265,848 | 5/1981 | Rüsch | 264/173 |
| 4,276,250 | 6/1981 | Satchell et al. | 264/167 |
| 4,282,876 | 8/1981 | Flynn | 128/349 R |
| 4,283,447 | 8/1981 | Flynn | 428/36 |
| 4,306,562 | 12/1981 | Osborne | 128/348 |
| 4,321,226 | 3/1982 | Markling | 264/149 |
| 4,323,071 | 4/1982 | Simpson et al. | 128/343 |
| 4,330,497 | 5/1982 | Agdanowski | 264/150 |
| 4,430,083 | 2/1984 | Ganz et al. | 604/283 |
| 4,495,134 | 1/1985 | Ouchi et al. | 264/512 |
| 4,551,292 | 11/1985 | Fletcher et al. | 264/173 |

FOREIGN PATENT DOCUMENTS

| | | | |
|---|---|---|---|
| 58-11118 | 1/1983 | Japan | 264/173 |
| 1349843 | 4/1974 | United Kingdom | 264/173 |
| 1370281 | 10/1974 | United Kingdom | 425/132 |

*Primary Examiner*—Jeffery Thurlow
*Attorney, Agent, or Firm*—Lockwood, Alex, Fitzgibbon & Cummings

[57] ABSTRACT

A thin-walled guiding catheter of the type having a distal end adapted to be formed into curved configurations and passed through branching blood vessels and the like is prepared with a three-layered tubular body portion having a lubricious inner sheath defining a lubricious guiding lumen, a rigid intermediate sheath, and a flexible outer sheath, which may be radiopaque. The distal tip portion thereof has a similar construction, but from which the rigid intermediate sheath is omitted. The guiding catheter exhibits excellent torque response and control while being especially thin-walled, thereby permitting minimization of the outer diameter size while permitting passage of an intravascular catheter and the like through its lumen.

7 Claims, 8 Drawing Figures

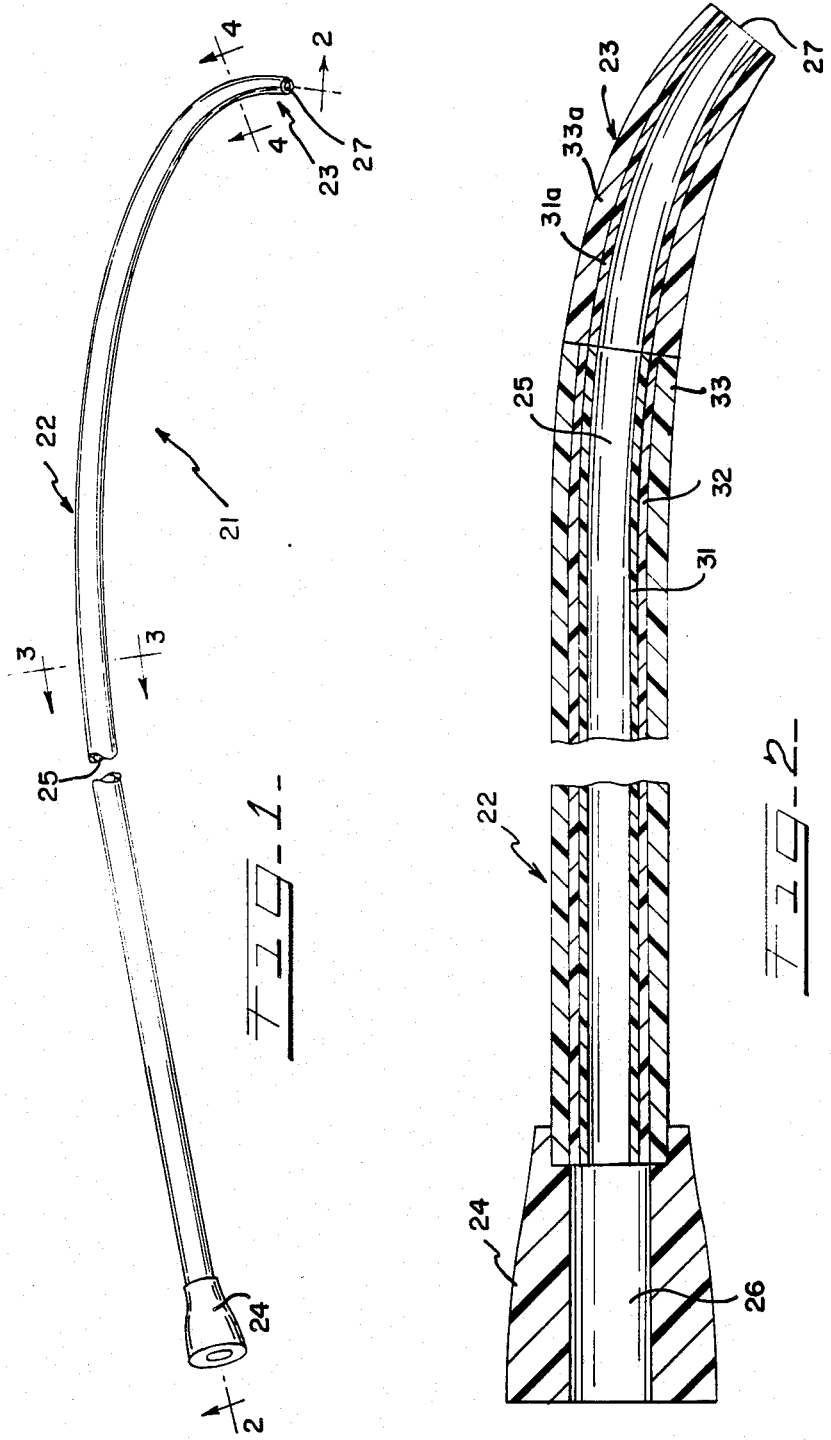

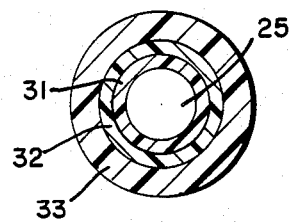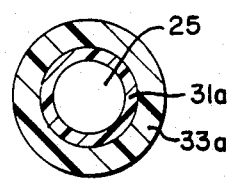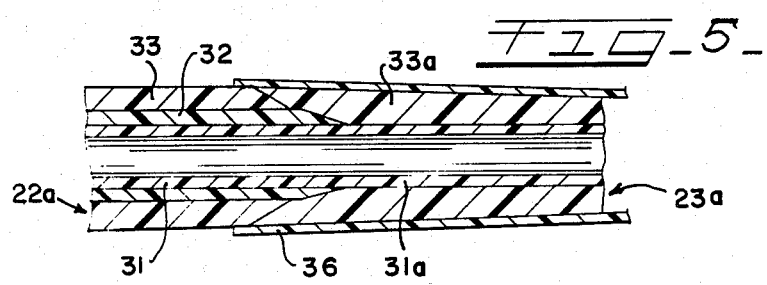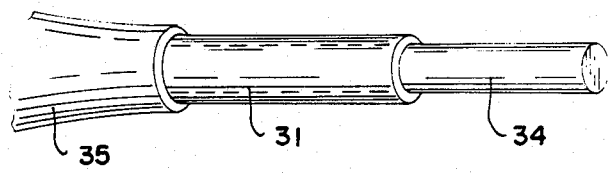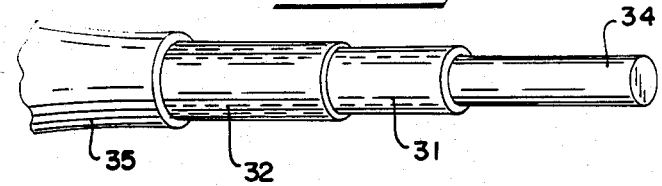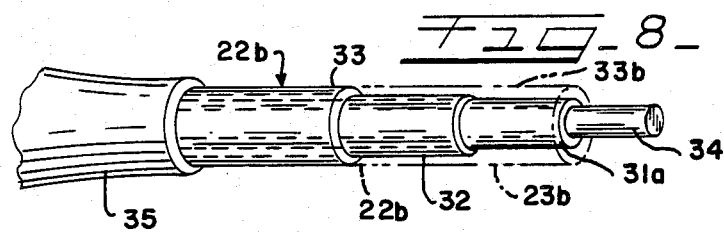

PREPARING GUIDING CATHETER

This is a continuation-in-part of application Ser. No. 587,382, filed Mar. 8, 1984, now U.S. Pat. No. 4,596,563 issued Jun. 24, 1986 and of application Ser. No. 587,557, filed Mar. 8, 1984, each of which is a continuation-in-part of application Ser. No. 502,526, filed June 9, 1983, now abandoned.

BACKGROUND AND DESCRIPTION OF THE INVENTION

The present invention generally relates to a guiding catheter and method for making the same, and more particularly to a guiding catheter that has a lubricious lumen and that is thin-walled while still exhibiting excellent strength characteristics, the thin-walled construction being one in which the elongated body of the catheter includes a thin flexible outer sheath that overlies a thin rigid intermediate sheath which in turn overlies a third, interior sheath that provides the lubricious lumen. The guiding catheter further includes a flexible, atraumatic tip portion located at one end of the elongated tubular member, which tip portion has a structure similar to the elongated body portion but which does not include the rigid intermediate layer.

Guiding catheters are well-known for use in diagnostic and therapeutic applications wherein they are used to provide a guiding lumen through which a treating catheter such as an intravascular catheter or the like is passed such that the treating catheter may be used to administer a fluid to, or otherwise contact such as with a balloon, a precise location within the cardiovascular system. In order to accomplish this, the guiding catheter must be able to traverse a pathway through, for example, branching blood vessels. Prior to insertion of the treating catheter through the guiding lumen of the guiding catheter, the guiding catheter is positioned in the vicinity of the administration or treatment location, this positioning being accomplished in part by manipulation of a proximal portion of the guiding catheter in order to impart forces needed to curve and guide the guiding catheter through the curving and branching blood vessels, at times in association with a very small diameter elongated flexible guide wire.

Typical assemblies including a guiding catheter and a treating catheter are assemblies used for percutaneous transluminal coronary angioplasty. In such systems or assemblies, it is important that the guiding catheter, as well as the treating catheter, exhibit adequate torque control while at the same time having a substantially atraumatic tip. One such guiding catheter structure is made by extruding a thin base coat of a polyfluoroethylene, such as Teflon materials available from E.I. duPont de Nemours & Co., Inc., over a mandrel, after which a braided material, which may be metal wire, is positioned thereover, and coated with a flexible material. Braided guiding catheters of this type do not always provide the exceptional degree of torque control that is desired for guiding catheters of the intravascular type, and they may also exhibit a somewhat excessively stiff tip portion. Good torque control is exhibited when slow rotation of the hub end of a catheter is translated to the tip or distal end without "whipping", which is characterized by a temporary lag in movement followed by a rapid rotation.

Other guiding catheters that are especially useful in assemblies for percutaneous transluminal recanalization of chronic arterioschlerotic obstructions by catheterization techniques are of structure that includes an inner hose having a surface layer of synthetic fiber fabric such as a Nylon (duPont trademark) polyamide, which is covered by a protective hose of a material such as a fluoroethylenepropylene that is heat shrunk therearound. Another guiding catheter provides a tetrafluoroethylene polymer tubular member that is encased within a heat shrunk flexible tubular member made of a modified polyolefin.

Because these guiding catheters are used in an intravascular manner, they must have an extremely small outside diameter, while still providing an inside diameter or lumen size that is adequate to permit the passage of the treating catheter therethrough. Furthermore, since these catheters come into contact with living tissue, including organs such as the heart, it is extremely important that the guiding catheter be in place for a minimal length of time. Overall insertion time includes the length of time needed to feed the guiding catheter through a cardiovascular system and then feed the treating catheter through the lubricious lumen of the guiding catheter. Such insertion time can be better controlled if the guiding catheter is stiff enough to be resistant to the formation of kinks therein, while at the same time possessing enough flexibility to be responsive to maneuvering forces and to provide adequate torque control when the guiding catheter is manipulated in conjunction with feeding same through a somewhat tortuous path. At the same time, the guiding catheter, particularly its distal end or tip portion, should be as atraumatic as possible.

The present invention provides a guiding catheter that meets these needs and objectives by virtue of its having a multi-layered structure which includes an innermost layer of a highly lubricious material, onto which is coated a thin, rigid intermediate layer which exhibits strength and stiffness properties that are extremely advantageous for an intravascular guiding catheter while still having adequate flexibility in its thin-walled sheath condition to permit the flexibility required of such a catheter. Closely overlying, and typically extruded onto, the rigid intermediate sheath is a flexible, thin-walled outer sheath that is compatible with the intermediate sheath and that, as a layer over the rigid intermediate sheath, imparts improved atraumatic properties to the longitudinal extent of the catheter and contributes to the overall flexibility of the guiding catheter, while also providing convenient opportunities to impart radiopaque properties to the catheter. While these guiding catheters may be produced such that a separate tip member is secured to the distal end of the body of the guiding catheter, it is preferred that the guiding catheter be structured in a manner such that the interior, lubricious sheath is an integral, one-piece continuous sheath that extends through both the body portion and the tip portion.

It is accordingly a general object of the present invention to provide an improved guiding catheter that is particularly well-suited for intravascular uses.

Another object of the present invention is to provide a thin-walled, multi-layered catheter that is especially suitable for use as a guiding catheter in conjunction with highly delicate treatments and diagnostic procedures including coronary angiography, coronary angioplasty, ventricular and/or aortic flush injections, and other similar procedures within the cardiovascular system.

Another object of this invention is to provide an improved thin-walled guiding catheter and method of making same which include positioning a highly lubricious lumen within a guiding catheter exhibiting excellent torque control. Another object of the present invention is to provide an improved guiding catheter and method by which the body portion and the tip portion thereof share a continuous, one-piece lubricious interior sheath.

Another object of the present invention is to provide an improved thin-walled guiding catheter that has a multi-layered construction of extruded material and that does not require adding any braiding or strands of strengthening material therebetween.

Another object of this invention is the utilization of a relatively rigid material in a thin-walled form within an elongated guiding catheter suitable for intravascular uses.

Another object of the present invention is to provide an improved intravascular guiding catheter that exhibits excellent torque response or control and that is particularly resistant to kinking, while still possessing the atraumatic properties and thinness needed for an intravascular catheter.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a perspective view, partially broken away, of a guiding catheter according to this invention;

FIG. 2 is a longitudinal sectional view, generally along the line 2—2 of FIG. 1;

FIG. 3 is a transverse sectional view along the line 3—3 of FIG. 1;

FIG. 4 is a transverse sectional view along line 4—4 FIG. 2;

FIG. 5 is a longitudinal sectional view along the section of the preferred guiding catheter at which the body portion ends and the tip portion begins;

FIG. 6 is a perspective view illustrating extrusion of the innermost, lubricious sheath according to this invention;

FIG. 7 is a perspective view illustrating the extrusion of the intermediate, rigid sheath over the lubricious sheath; and FIG. 8 is a perspective view illustrating extrusion of the outermost, flexible sheath over the intermediate, rigid sheath and illustrating, in phantom, a alternative assembly technique.

DESCRIPTION OF THE PARTICULAR EMBODIMENTS

FIG. 1 provides an illustration of the type of guiding catheter, generally designated as 21, within which this invention is embodied. Guiding catheter 21 includes an elongated tubular body portion 22, a tip portion 23, and a hub 24. A longitudinal lumen 25 extends throughout the elongated tubular body 22 and the tip portion 23, such longitudinal lumen 25 extending from a generally coaxial bore 26 in the hub 24 to a distal orifice 27 within the tip portion 23. Lubricious lumen 25 is sized and structured to facilitate passage completely therethrough of an appropriate intravascular catheter or the like (not shown), which would have an outer diameter on the order of a "French 5" size, which is approximately 0.008 inch.

Elongated body 22 includes an interior sheath 31, an intermediate, generally rigid sheath 32, and a flexible outer sheath 33. Each sheath 31, 32 and 33 is extremely thin-walled to the extent that the elongated tubular body 22 is itself thin walled in order that the lubricious lumen 25 may be as large in diameter as possible while minimizing the outside diameter of the body 22. Tip portion 23 includes an interior, lubricious sheath 31a over which a flexible outer sheath 33a is positioned.

Interior sheath 31,31a is made of a material exhibiting superior lubricity, preferably a Teflon (duPont trademark) fluoroethylene polymer, such as polytetrafluoroethylene (PTFE), fluoroethylene copolymers having pendant perfluoro alkoxy groups (PFA), copolymers of tetrafluorethylene and hexafluoropropylene (FEP), and copolymers of ethylene and tetrafluoroethylene (Tefzel). Especially preferred because of its superior lubricity and relative ease of extrusion is the PFA type of fluoroethylene polymer, which is a derivative of polytetrafluoroethylene that exhibits pendant perfluoro alkoxy groups. These fluoroethylene polymers exhibit the following basic structure:

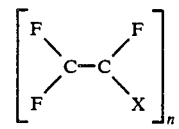

wherein X is fluorine, hydrogen or OR, wherein R is fluoroalkyl such as a fluoromethane, and wherein n is on the general order of 1000.

Intermediate sheath 32 is made of a material that, after extrusion, is substantially stiff, and, in combination with the interior sheath 31 and the flexible outer sheath 33, provides the advantageous torque control properties that are characteristic of this invention. Rigid intermediate sheath 32 is an extrusion grade polymeric cylinder that had been formed by extrusion, preferably onto a precision mandrel 34, which is typically a silver wire or the like. Precision mandrel 34 is illustrated generally in FIGS. 6, 7 and 8, which also depict an outlet die 35 of an extruder. Typically, such rigid polymeric materials will have a hardness between approximately Shore D75 and Shore D85.

Typical suitable polymeric materials out of which rigid intermediate sheath 32 can be extruded include polycarbonates, polyethylene terephthalate (PET), polyethylene terephthalate glycol (PETG), polyamides such as Nylon, which is a trademark of duPont, polyacetal copolymers, such as Celcon (trademark) copolymers of Celanese Corp., acetal homopolymers such as Delrin (trademark) polymers of duPont, and the like.

Flexible outer sheath 33 is a polymeric material that had been extruded as a sheath over the intermediate sheath 32. Such flexible outer sheath 33 is made of a flexible polymeric material that is biocompatible. Exemplary suitable materials include soft polyurethanes, soft polyesters, low density polyethylene, and the like. An example of a suitable flexible polyester is Hytrel, an ester of polytetramethylene glyco and adipic acid with 1,4-butanediol as a chain extender. Typically, these flexible polymeric materials will have a hardness between approximately Shore D40 and Shore D60. Polyurethanes are the preferred materials out of which the flexible outer sheath 33 is made.

Tip portion 23 is designed to minimize intimal trauma. Generally, its interior sheath 31a is made of the same material as the interior sheath 31 of the tubular body 22, while the flexible outer sheath 33a thereof is preferably made of the same material as the flexible outer sheath 33 of the tubular body 22. Because the tip portion 23 excludes the more rigid, stiffening intermediate sheath 32, the tip portion 23 is particularly movable, flexible and atraumatic.

Tip portion 23 may be an initially separate member that is affixed to the elongated tubular body 22 by suitable means, such as by heating, by other energy sources, and/or by adhesives or the like. FIG. 2 depicts this type of assembly of these two separate components. Such assembly can be assisted by the use of a length of shrinkable tubing that is placed over the joint location prior to and during the assembly operation in order to enhance the smoothness and strength of the joint.

The preferred manner of forming the tip portion 23 first provides a three-layered tubular body 22 that has a total length of that desired for the completed guiding catheter 21. A distal end section, typically on the order of four to five inches in length, of the flexible outer sheath 33 is removed by convenient means, such as by grinding or other treatment. A length of intermediate sheath 32 is thus exposed for removal thereof. Especially efficient and effective removal of the intermediate sheath 32 is effected by treating same with a solvent therefor that will not dissolve away the interior sheath 31 thereunder. Suitable solvents in this regard include methyl ethyl ketone, pyrrole derivatives, and the like. This procedure results in providing a tubular body 22a (FIG. 5) which includes the interior sheath length 31a of the tip portion 23 that is continuous with and is the same integral extrudate as is the interior sheath 31 of the tubular body 22a.

Thereafter, as illustrated in FIG. 5, a length of flexible outer sheath 33a is secured onto and over the thus exposed interior sheath length 31a. A preferred manner of accomplishing this result includes sliding a length of flexible outer sheath tubing 33a over the exposed interior sheath length 31a, such flexible outer sheath tube length 33a having an internal diameter that is only very slightly larger than the external diameter of the exposed interior sheath length 31a, such interior diameter being just adequate to permit the flexible outer sheath tube length 33a to be slid and/or twisted over the interior sheath 31a. Appropriate adhesive material may be interposed therebetween. Superior assembly is enhanced by utilizing a length of shrinkable tubing 36 over the flexible outer sheath tube length 33a in accordance with generally known procedures in order to provide substantially uniform inwardly radially directed forces to insure a secure assembly. This procedure is particularly advantageous in view of the difficulty of fusing or otherwise assembling interior sheath 31 to a separate interior sheath 31a, especially when using highly resistant materials such as a Teflon material, since by this approach, the interior sheath 31 and interior sheath length 31a are a single-piece, unitary tubing or sheath.

An alternative, substantially fuseless procedure is illustrated in FIG. 8, wherein the tip portion 23b includes the continuous, single-piece interior sheath, 31,31a on the order of that sheath of the embodiment illustrated in FIG. 5, while also including a continuous, single length flexible outer sheath 33,33b. In effect, tip portion 23b is provided as an integral extension of the flexible outer polymeric sheath 33, as well as of the lubricious interior sheath 31. This is accomplished by extruding the interior sheath 31,31a as a single continuous tube directly onto the precision mandrel 34, extruding rigid intermediate sheath 32, and thereafter extruding the flexible outer sheath length 33b directly onto the interior sheath length 31a, while continued extrusion in this regard results in the flexible outer sheath 33 being extruded onto the intermediate sheath 32 as a unitary, single-piece extension of the flexible outer sheath length 33b. A particularly advantageous manner of accomplishing this alternative procedure is as follows.

Interior sheath 31,31a is extruded onto the precision mandrel 34. The rigid intermediate sheath 32 is modified so as to impart a gap having an axial length substantially equal to the length of the tip member 23b to be formed. If desired, a series of intermittent gaps between lengths of rigid intermediate sheath 32 can be formed by intermittently stopping the extrusion flow of the rigid intermediate sheath polymer from the outlet die 35. A layer of flexible outer sheath polymer is then extruded over the thus gapped rigid polymer sheath 32, as well as over the intermediate gap(s) therebetween in order to thereby extrude the flexible outer polymeric material as an integral length that alternately overlies the rigid polymer intermediate sheath 32 and the interior sheath length 31a. The portion of this flexible polymer extrusion that overlies the rigid polymer intermittent sheath 32 completes the formation of the elongated tubular body 22b of this embodiment, while the portion of this flexible polymer extrusion that overlies the interior sheath length 31a combines with such interior sheath length 31a to form the tip portion 23b of this embodiment. If a plurality of gaps were formed during this extrusion, then appropriate severance is accomplished in order to sever the distal end of the tip portion 23b from the proximal end of an adjacent tubular body portion 22b.

With more particular reference to the modification of the intermediate sheath 32 so as to impart one or more gaps therein, at least two different general approaches may be taken. One includes removal of a length of the intermediate sheath 32, and the other includes extruding the intermediate sheath 32 in an intermittent manner. When proceeding by the removal approach, the intermediate sheath 32 is extruded continuously over the interior sheath 31,31a, and the removal is effected in any convenient manner, including mechanical cutting, grinding, solvent dissolving and ultrasonic removal (typically preceeded by freezing). A removal approach is included within the preferred assembly procedure described hereinabove. When proceeding by the intermittent extrusion approach, extrusion of the intermediate sheath polymer proceeds until the needed body length of intermediate sheath 32 has been coated over the interior sheath 31, at which time this extruding is interrupted or stopped while the mandrel 34 and the tip length interior sheath 31a proceed to move beyond the outlet die 35 in order to form a gap in the intermediate sheath 32, after which the extrusion resumes until another body length of intermediate sheath 32 coats the body length interior sheath 31. Whether the removal approach or the intermittent extrusion approach is used, the unitary, single-piece flexible polymer outer sheath 33,33b is then coated over the intermediate sheath(s) 32 and over the gap(s), as generally illustrated in phantom in FIG. 8. The intermittent extrusion approach provides the possibility for simultaneous coextrusion of the interior sheath 31,31a of the intermediate sheath 32, and of the flexible outer sheath 33,33b.

In order to be suitable for use in procedures utilizing radiological techniques, the guiding catheter 21 should be radiopaque. An exemplary manner of imparting this property to guiding catheter 21 is to utilize a flexible polymeric material for the outer sheath 23 that includes a radiopaque agent, such as barium sulfate, bismuth subcarbonate or the like. This approach provides what can be an advantageous feature for many uses, which is that the tip portion 23 will be more visible by radiological techniques than the rest of the guiding catheter 21, such enabling the user to more easily focus on manipulations needed to maneuver the tip portion through the cardiovascular system.

With more particular reference to details of the extrusion method, the interior sheath 31 is extruded onto the precision mandrel 34 for a thickness of between about 0.003 inch and 0.005 inch at a temperature of between about 350° and 450° F. Preferably, this extrusion is then pretreated with an etching solution, such as Polyetch, (a trademark of Matheson). Next, the intermediate sheath polymer is extruded over the interior sheath 31, also at a temperature of between about 350° and 400° F. At these elevated temperatures, the rigid intermediate material forms a bond with the interior sheath. At a temperature between about 300° and 350° F., the flexible outer sheath coating is extruded thereover. At the tip portion, the flexible outer sheath is bonded to the interior sheath. Extrusion at elevated temperatures softens the surface of the sheath onto which a subsequent layer is being extruded in order to enhance the extent that the respective sheaths are combined and generally adhered together in order to form a more unitary body that will be especially responsive to torque forces imparted thereto and will exhibit advantageous thin-walled properties.

With reference to the hub 24, such will typically be joined the proximal end of the elongated tube or body 22 by a suitable material, such as an adhesive solvent that is a solvent which will soften the materials utilized and adhere the hub 24 to the tubular body 22. Typical solvents in this regard include tetrahydrofuran, methyl ethyl ketone, acetone, and the like. Hub 24 is of a structure that is suitable for the particular desired use of the guiding catheter 21. Also associated with the hub 24 may be a manipulator device (not shown) of generally known construction for rotating and/or deflecting the guiding catheter 21 as desired in order to assist in threading the tip portion 23 thereof through branching blood vessels and the like.

An exemplary guiding catheter 21 prepared according to this invention is one in which its lubricious lumen 25 has an inner diameter that is able to slidingly receive and have passed therethrough an intravascular catheter of the "French 5" size. The total wall thickness of the tubular body 22 of the guiding catheter 21 would typically be on the order of 0.008 inch to 0.01 inch, composed of between about 0.0005 to 0.003 inch as the lubricious interior sheath 31, between about 0.0035 and 0.005 inch as the rigid intermediate sheath 32, and between about 0.0045 and 0.003 inch as the flexible outer sheath 33.

It will be understood that the embodiments of the present invention which have been described are merely illustrative of a few of the applications of the principles of the present invention. Numerous modifications may be made by those skilled in the art without departing from the true spirit and scope of the invention.

We claim:

1. A method of making a guiding catheter having a distal end adapted to be formed into curved configurations and passed through branching blood vessels and having a longitudinal lumen therethrough for receiving an intravascular catheter and the like, the method comprising:

forming a continuous and uninterrupted longitudinal lubricious interior sheath coating onto a mandrel;

extruding a generally rigid intermediate sheath radially over the lubricious interior sheath;

coating a generally flexible outer sheath radially over the generally rigid intermediate sheath;

removing a distal end axial length of said generally flexible outer sheath;

removing a distal end axial length of said generally rigid intermediate sheath and thereby exposing a distal end axial length of said lubricious interior sheath; and securing a length of generally flexible outer sheath onto and over said exposed distal end axial length of the continuous and uninterrupted longitudinal lubricious interior sheath to thereby form a two-layered atraumatic distal end tip portion that is an axial length of generally flexible outer sheath secured onto the exposed distal end axial length of the continuous lubricious interior sheath.

2. The method according to claim 1, wherein said step of removing the distal end length of the generally flexible outer sheath includes using an abrasive member.

3. The method according to claim 1, wherein said step of removing the distal end length of the generally rigid intermediate sheath includes using a solvent.

4. A fuseless method of making a guiding catheter having a distal end adapted to be formed into curved configurations and passed through branching blood vessels and having a longitudinal lumen therethrough for receiving an intravascular catheter and the like, the method comprising:

coating a continuous and uninterrupted longitudinal lubricious interior sheath coating onto a mandrel;

extruding a longitudinal axially gapped generally rigid intermediate sheath radially over the lubricious interior sheath coating, wherein said extruding step includes providing a longitudinal axial gap and a longitudinal axial length of the generally rigid intermediate sheath, said longitudinal axial gap exposing an axial length of the lubricious interior sheath coating; and extruding a generally flexible outer sheath coating radially over the longitudinal axially gapped generally rigid intermediate sheath and the continuous and uninterrupted interior sheath, said extruding step laying down a continuous and uninterrupted flexible polymer elongated sheath over said longitudinal axial gap to form a two-layered atraumatic distal end tip that is an axial length of generally flexible outer sheath radially positioned over the exposed length of the lubricious interior sheath coating, and the continuous and uninterrupted flexible polymer elongated sheath laid down by said extruding step is continuously laid down over said longitudinal axial length of the generally rigid intermediate sheath to form a tubular body integral with said atraumatic distal end tip without fusing said atraumatic distal end tip to said tubular body.

5. The fuseless method according to claim 4, wherein said step of forming the longitudinally gapped generally rigid intermediate sheath is carried out by intermittently extruding the generally rigid intermediate sheath.

6. The fuseless method according to claim 4, wherein said step of forming the longitudinally gapped generally rigid intermediate sheath includes continuously extruding the generally rigid intermediate sheath and removing a longitudinal gap length of the generally rigid intermediate sheath.

7. The fuseless method according to claim 4, wherein said lubricious interior sheath coating, said generally rigid intermediate sheath and said generally flexible outer sheath are coextruded.

* * * * *